US011164657B2

(12) United States Patent
Nagarajan et al.

(10) Patent No.: US 11,164,657 B2
(45) Date of Patent: Nov. 2, 2021

(54) ACCELERATED PHARMACEUTICAL REPURPOSING BY FINDING ANTICORRELATIONS AND BY TEXT MINING

(71) Applicant: INTERNATIONAL BUSINESS MACHINES CORPORATION, Armonk, NY (US)

(72) Inventors: Meenakshi Nagarajan, San Jose, CA (US); Alix Lacoste, Brooklyn, NY (US)

(73) Assignee: International Business Machines Corporation, Armonk, NY (US)

( * ) Notice: Subject to any disclaimer, the term of this patent is extended or adjusted under 35 U.S.C. 154(b) by 922 days.

(21) Appl. No.: 15/826,792

(22) Filed: Nov. 30, 2017

(65) Prior Publication Data
US 2019/0163869 A1 May 30, 2019

(51) Int. Cl.

| | |
|---|---|
| G16B 40/00 | (2019.01) |
| G06F 16/33 | (2019.01) |
| G16H 10/20 | (2018.01) |
| G16B 20/00 | (2019.01) |
| G16H 20/10 | (2018.01) |
| G16H 70/40 | (2018.01) |
| G16B 5/00 | (2019.01) |
| G16B 25/10 | (2019.01) |
| G16B 35/20 | (2019.01) |
| G01N 33/50 | (2006.01) |
| C12Q 1/02 | (2006.01) |
| G01N 21/64 | (2006.01) |
| G16B 50/00 | (2019.01) |

(52) U.S. Cl.
CPC ............ *G16B 40/00* (2019.02); *C12Q 1/025* (2013.01); *G01N 33/5023* (2013.01); *G06F 16/334* (2019.01); *G16B 5/00* (2019.02); *G16B 20/00* (2019.02); *G16B 25/10* (2019.02); *G16B 35/20* (2019.02); *G16H 10/20* (2018.01); *G16H 20/10* (2018.01); *G16H 70/40* (2018.01); *G01N 21/6486* (2013.01); *G06F 2216/03* (2013.01); *G16B 50/00* (2019.02)

(58) Field of Classification Search
None
See application file for complete search history.

(56) References Cited

U.S. PATENT DOCUMENTS

| | | |
|---|---|---|
| 8,571,804 B2 | 10/2013 | Cohen et al. |
| 8,725,552 B2 | 5/2014 | Hyde et al. |
| 9,536,193 B1 | 1/2017 | Labrie |
| 9,886,665 B2 | 2/2018 | Chen |
| 2005/0060305 A1 | 3/2005 | Hopkins et al. |
| 2014/0046962 A1 | 2/2014 | Chen |
| 2015/0227700 A1 | 8/2015 | Bundela et al. |

FOREIGN PATENT DOCUMENTS

WO 2009027843 A2 3/2009

OTHER PUBLICATIONS

Napolitano, Francesco, et al. "Drug repositioning: a machine-learning approach through data integration." Journal of cheminformatics 5.1 (2013): 30.*
Andronis, Christos, et al. "Literature mining, ontologies and information visualization for drug repurposing." Briefings in bioinformatics 12.4 (2011): 357-368.*
Tari, Luis B., and Jagruti H. Patel. "Systematic drug repurposing through text mining." Biomedical Literature Mining. Humana Press, New York, NY, 2014. 253-267.*
Spampinato et al., "BioWizard: Discovering and validating associations between biological entities by integrated analysis of scientific literature and experimental data", Conference Paper, Proceedings of the IEEE Symposium on Computer-Based Medical Systems, https://www.researchgate.net/publication/261381536, Jun. 2012, pp. 1-7.
Barcante et al., "Identifying Drug Repositioning Targets Using Text Mining", https://www.researchgate.net/publication/265376239, conference paper, Oct. 2014, pp. 1-8.
Jin et al., "Toward better drug repositioning: prioritizing and integrating existing methods into efficient pipelines", Published in final edited form as: Drug Discov Today. May 2014 ; 19(5): 637-644. doi:10.1016/j.drudis.2013.11.005, pages 1-18.
Faro et al., "Discovery and assessment of gene-disease associations by integrated analysis of scientific literature and microarray . . . ", https://www.researchgate.net/publication/224211859, conference paper, Dec. 2010, pages 1-6.
Mina et al., "Common disease signatures from gene expression analysis in Huntington's disease human blood and brain", Orphanet Journal of Rare Diseases (2016), pp. 1-13.
Jurca et al., "Integrating text mining, data mining, and network analysis for identifying genetic breast cancer trends", BMC Res Notes (2016), pp. 1-35.

(Continued)

*Primary Examiner* — G Steven Vanni
(74) *Attorney, Agent, or Firm* — Caleb D. Wilkes

(57) ABSTRACT

Utilizing a computing device to assist in repurposing of a pharmaceutical. An identification of a pharmaceutical for repurposing study is received by a computing device. A pharmaceutical expression signature is retrieved based upon the identification of the pharmaceutical, the pharmaceutical expression signature indicating differential expressions of a plurality of biomolecules regulated by the pharmaceutical. A plurality of disease expression signatures are retrieved from a disease omics database, each disease expression signature indicating differential expressions of a plurality of biomolecules affected by a disease. A pharmaceutical vector is generated based upon the pharmaceutical expression signature for the pharmaceutical. A plurality of disease vectors are generated based upon the plurality of disease expression signatures for each disease. N hypotheses correlating the pharmaceutical vector and one or more of the plurality of disease vectors are generated, each hypothesis indicating a potential repurposing for the pharmaceutical to treat the disease.

20 Claims, 11 Drawing Sheets

(56) References Cited

OTHER PUBLICATIONS

Lekka et al, "Literature analysis for systematic drug repurposing: a case study from Biovista", Elsevier, Drug Discovery Today: Therapeutic Strategies, vol. 8, No. 3-4 2011, pp. 103-108.
Faro et al., "Combining literature textmining with microarray data: advances for system biology modeling", Briefings in Bioinformatics. vol. 13. No. 61/\ 82, Advance Access published on Jun. 15, 2011, pp. 1-22.
Mell et al., "The NIST Definition of Cloud Computing", National Institute of Standards and Technology, Special Publication 800-145, Sep. 2011, pp. 1-7.
Glenisson et al., "Meta-Clustering of Gene Expression Data and Literature-based Information", SIGKDD Explorations, vol. 5, Issue 2, 2003, pp. 101-112.

\* cited by examiner

ACCELERATED PHARMACEUTICAL REPURPOSING BY FINDING ANTICORRELATIONS AND BY TEXT MINING

BACKGROUND

The present invention relates generally to the field of pharmaceutical repurposing, and more particularly to accelerated pharmaceutical repurposing utilizing omics data and literature text mining.

BRIEF SUMMARY

Embodiments of the present invention disclose a method, system, and computer program product for utilizing a computing device to assist in repurposing of a pharmaceutical. An identification of a pharmaceutical is received by a computing device for repurposing study. The computing device retrieves a pharmaceutical expression signature for the pharmaceutical based upon the identification of the pharmaceutical, the pharmaceutical expression signature indicating differential expressions of a plurality of biomolecules regulated by the pharmaceutical versus a control. The computing device retrieves a plurality of disease expression signatures from a disease omics database, each disease expression signature indicating differential expressions of a plurality of biomolecules affected by a disease versus the control. A pharmaceutical vector is generated by the computing device based upon the pharmaceutical expression signature for the pharmaceutical. A plurality of disease vectors are generated by the computing device based upon the plurality of disease expression signatures for each disease. N hypotheses are generated correlating the pharmaceutical vector and one or more of the plurality of disease vectors, each of the N hypotheses generated when an anticorrelation exists between the pharmaceutical expression signature and one or more disease expression signatures of the plurality of disease expression signatures. Each hypothesis indicates a potential repurposing for the pharmaceutical to tread the disease.

DETAILED DESCRIPTION

Figure 1:
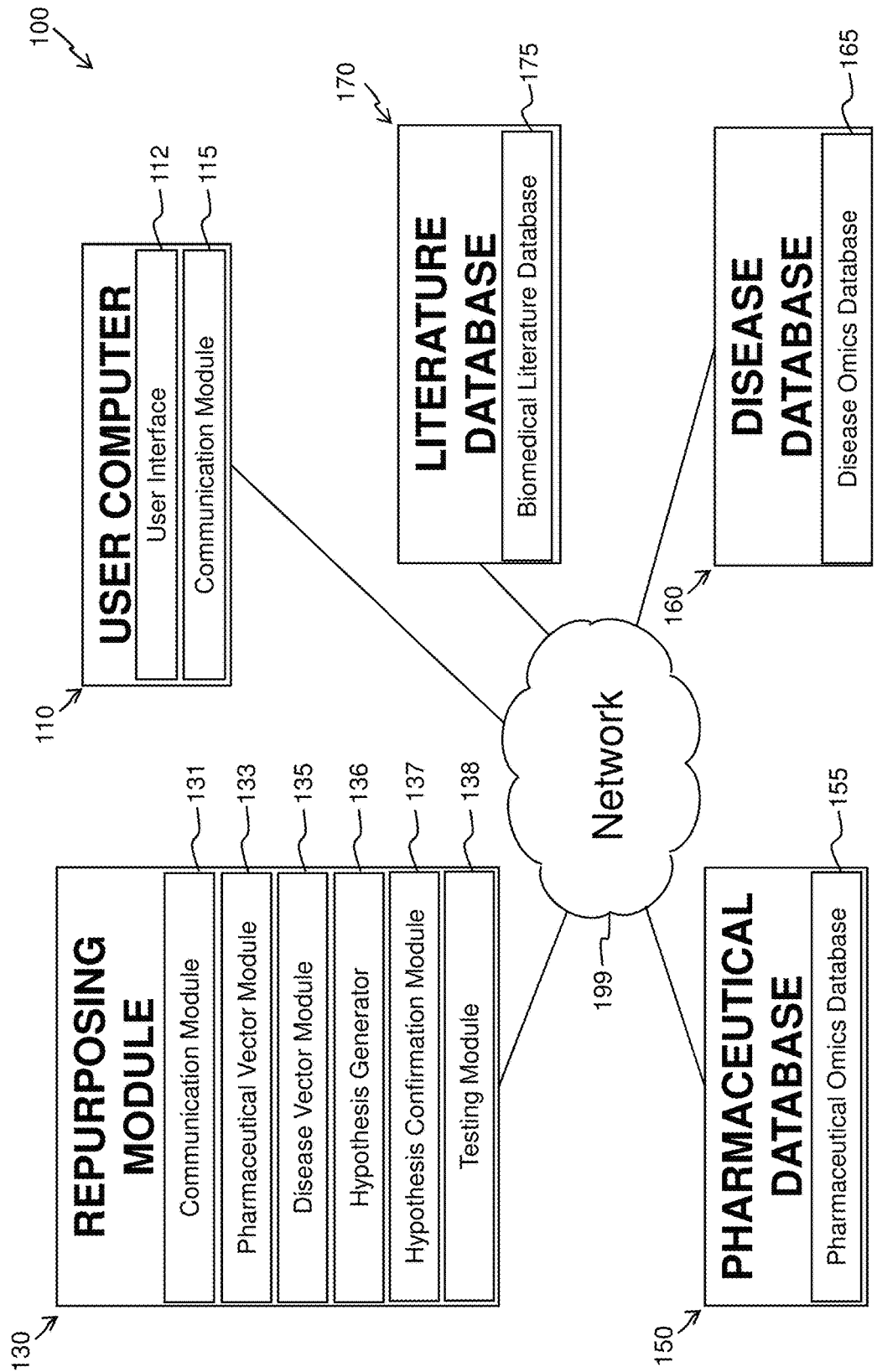
FIG. 1 is a functional block diagram illustrating an environment for accelerated pharmaceutical repurposing, in accordance with an embodiment of the present invention.

Pharmaceutical repurposing (also known as "repositioning," "re-profiling," "indication expansion," or "therapeutic switching") is the development of existing pharmaceuticals for new therapeutic indications. Repositioning known pharmaceuticals has many advantages over developing new pharmaceuticals, including greatly decreasing cost associated with development, lessened safety concerns since the pharmaceutical has already undergone extensive clinical testing, and therefore significant acceleration in treatment of novel therapeutic areas. Traditional approaches to pharmaceutical repositioning involve use of assays, which are both time-consuming and costly. Computational approaches offer the opportunity to greatly reduce or eliminate the assay process. Presented is a method, system, and computer program product for accelerated pharmaceutical repurposing utilizing omics data and literature text mining.

Computational approaches for pharmaceutical repurposing as described herein involve literature text mining utilizing the considerable body of biomedical literature which has developed over time regarding known pharmaceuticals as well as known diseases or conditions. This body of biomedical literature, including scientific articles, clinical trials, patents, and otherwise is simply more massive than any human being could process in a lifetime, while modern computational approaches using natural language processing combined with machine learning present an opportunity to process this body of literature in a realistic time frame. Text mining of biomedical literature, such as described herein, is specifically applied to pharmaceutical repurposing, but also has applications in drug discovery (using text mining to show support for gene expression data suggesting disease or conditions), determining suggested mechanisms of action (since gene expression data merely gives a list of genes up-regulated and down-regulated, and text mining can show interplay between the genes and suggest a biological pathway or mechanism of action), and precision medicine (using individual patient omics data (such as genomic) combined with literature text mining to propose pharmaceuticals specifically tailored to the patient's profile).

"Omics data," as used herein, refers to quantification of levels of genes, proteins, and metabolites corresponding to genomics, proteomics or metabolomics (collectively, "biomolecules"). Most commonly, omics data reflects gene expression. In the present invention, by examining biomolecules that have differential expressions from a control, based upon pharmaceuticals or diseases, it may be possible to obtain a pharmaceutical expression signature or a disease expression signature indicating which biomolecules are up-regulated and which are down-regulated by the pharmaceutical or disease. This "omics data" may be utilized in the present invention by seeking an inverse relationship (also known as an "anticorrelation") between the pharmaceutical expression signature and the disease expression signature. If a strong anticorrelation is found between the pharmaceutical signature and the disease signature, the repurposed pharmaceutical may potentially be a cure for the disease, since the pharmaceutical may return the biomolecules to their normal levels. The repurpose for the pharmaceutical may be further reviewed via text mining of a text database, as further discussed below.

FIG. 1 is a functional block diagram illustrating an environment 100 for accelerated pharmaceutical repurposing utilizing omics data and literature text mining, in accordance with an embodiment of the present invention. In various embodiments, a user associated with user computer 110 is interested in repurposing a pharmaceutical in the most efficient manner possible or seeking a treatment for a disease or a condition (referred to herein as a "disease" or collectively "diseases") using a repurposed pharmaceutical in the most efficient manner. The user computer 110 transmits an identification of the pharmaceutical (such as, for example, a trade name, a generic name, a chemical name, a chemical formula, or any other way of uniquely identifying the pharmaceutical) or an identification of the disease to repurposing module 130. The repurposing module 130, based upon data obtained from pharmaceutical database 150, disease database 160, and literature database 170, as further described herein, determines likely repurposing for the pharmaceutical or, alternatively, a pharmaceutical that may be repurposed for treatment of the identified disease, and transmits the results to the user computer 110. All of user computer 110, repurposing module 130, pharmaceutical database 150, disease database 160, and literature database 170 are connected via network 199.

In various embodiments, network 199 represents, for example, an internet, a local area network (LAN), a wide area network (WAN) such as the Internet, and includes wired, wireless, or fiber optic connections. In general, network 199 may be any combination of connections and protocols that will support communications between user computer 110, repurposing module 130, pharmaceutical database 150, disease database 160, and literature database 170, in accordance with an embodiment of the invention.

In various embodiments, user computer 110, repurposing module 130, pharmaceutical database 150, disease database 160, and literature database 170 may be, for example, a mainframe or a mini computer, a terminal, a laptop, a tablet, a netbook personal computer (PC), a mobile device, a desktop computer, or any other sort of computing device, in accordance with embodiments described herein. User computer 110, repurposing module 130, pharmaceutical database 150, disease database 160, and literature database 170 may include internal and external hardware components as depicted and described further in detail with reference to FIG. 4, below. In other embodiments, each of user computer 110, repurposing module 130, pharmaceutical database 150, disease database 160, and literature database 170 may be implemented in a cloud computing environment, as described in relation to FIGS. 5 and 6, below. In a still further embodiment, some or all of user computer 110, repurposing module 130, pharmaceutical database 150, disease database 160, and literature database 170 are embodied in physically the same computing device, with all communications between various components internally.

User computer 110, repurposing module 130, pharmaceutical database 150, disease database 160, and literature database 170, in effect, represent any sort of computing device possessing sufficient processing power to execute software for accelerated pharmaceutical repurposing utilizing omics data and literature text mining.

Computing devices associated with user computer 110, repurposing module 130, pharmaceutical database 150, disease database 160, and literature database 170 may utilize a hosted workload 96 as displayed in connection with FIG. 7 below, and/or perform other tasks as further described herein.

In the exemplary embodiment, the user computer 110 includes user interface 112 and communication module 115.

User interface 112 represents software and/or hardware for user at user computer 110 to enter (such as via keyboard 922) or select such as via a graphic user interface, in the preferred embodiment, a pharmaceutical for repurposing study. The user interface 112 will also display results of the repurposing study, as performed by the repurposing module 130, as further described herein. In the alternative embodiment, the user interface 112 allows a user to provide an identification of a disease for repurposing study. The user interface 112 also allows a user to select a number N of hypotheses that are to be generated by the repurposing module 130, each hypothesis indicating a potential repurposing of a pharmaceutical to treat a disease.

Communication module 115 represents software and/or hardware for user computer 110 to communicate with repurposing module 130. After the user at user computer 110, in the preferred embodiment, identifies the pharmaceutical for repurposing study or in the alternative embodiment identifies the disease for repurposing study, the communication module 115 transmits the identification of the pharmaceutical for repurposing study or the identification of the disease for repurposing study to the repurposing module 130. Hardware associated with communication module 115 may include a network adapter or interface 916, such as a TCP/IP adapter card or wireless communication adapter (such as a 4G wireless communication adapter using OFDMA technology) such as described below in connection with FIG. 5.

In the exemplary embodiment, repurposing module 130 includes communication module 131, pharmaceutical vector module 133, disease vector module 135, hypothesis generator 136, hypothesis confirmation module 137, and testing module 138.

Communication module 131 represents software and/or hardware to receive from the user computer 110, in the preferred embodiment, an identification of a pharmaceutical for repurposing study or, in the alternative embodiment, an identification of a disease for repurposing study. The identification of the pharmaceutical or the disease is further utilized as discussed herein. Hardware associated with communication module 115 may include a network adapter or interface 916, such as a TCP/IP adapter card or wireless communication adapter (such as a 4G wireless communication adapter using OFDMA technology) such as described below in connection with FIG. 5.

Pharmaceutical vector module 133 represents software for retrieving from the pharmaceutical database 150 pharmaceutical expression signatures for pharmaceuticals, which are used in the generation of pharmaceutical vectors. The pharmaceutical expression signatures indicate differential expressions of a plurality of biomolecules regulated by the pharmaceutical versus a control. The differential expression of the plurality of biomolecules regulated by the pharmaceutical indicate biomolecules up-regulated by the pharmaceutical and biomolecules down-regulated by the pharmaceutical. A sample pharmaceutical may, for example, up-regulate four genes and down-regulate six genes. The pharmaceutical vector module 133 utilizes the pharmaceutical expression signatures to generate pharmaceutical vectors. Each pharmaceutical vector is a list in computer-available form (such as a linked-list, spreadsheet, object etc.) of biomolecules affected by the pharmaceutical, for further use as discussed. With regard to the sample pharmaceutical, the pharmaceutical vector may include multiple entries indicating which proteins are up-regulated and which are down-regulated.

In the preferred embodiment, the pharmaceutical vector module 133 may retrieve a single pharmaceutical expression signature from the pharmaceutical database 150 for a pharmaceutical identified by the user computer 110 to generate a pharmaceutical vector to be matched against a plurality of disease vectors in determining possible repurposing. In the alternative embodiment, the pharmaceutical vector module 133 retrieves a plurality of pharmaceutical expression signatures from the pharmaceutical database 150 for generating a plurality of pharmaceutical vectors, to be matched against a single disease vector representing a disease identified by the user computer 110 in determining possible repurposing.

The disease vector module 135 represents software for retrieving from the disease database 160 disease expression signatures which are used in the generation of disease expression vectors. The disease expression signatures indicate differential expressions of a plurality of biomolecules affected by the disease versus a control (i.e. for a normal healthy human being or tissue sample). The differential expression of the plurality of biomolecules affected by the disease indicate biomolecules up-regulated by the disease and biomolecules down-regulated by the disease. A sample disease may, for example, down-regulate four proteins and up-regulate six proteins. The disease vector module 135 utilizes the disease expression signatures to generate disease vectors. Each disease vector may be a list in computer-available form (such as a linked-list, spreadsheet, object etc.) of biomolecules affected by the disease, for further use as discussed. With regard to the sample disease, the disease vector may include multiple entries indicating which proteins are up-regulated and which are down-regulated.

In the preferred embodiment, the disease vector module 135 retrieves a plurality of disease expression signatures from the disease database 160 for generating a plurality of disease vectors, to be matched against a single pharmaceutical vector representing a pharmaceutical identified by the user computer 110 in determining possible repurposing. In the alternative embodiment, the disease vector module 135 may retrieve a single disease expression signature from the disease database 160 for a disease identified by the user computer 110 to generate a disease vector to be matched against a plurality of pharmaceutical vectors in determining possible repurposing.

Hypothesis generator 136 represents software for correlation of pharmaceutical vectors and disease vectors to generate N hypotheses indicating a pharmaceutical may be an indication (i.e. treatment) for a given disease. As further discussed herein, in the presently disclosed invention, these N hypotheses are further confirmed via text mining, and in practice various levels of lab study are still required, followed by controlled study in humans, but the presently disclosed invention offers minimization of the amount of lab study required. N represents any number of hypotheses requested by user computer 110, the N hypotheses being the best match between pharmaceutical vectors and disease vectors correlated. A hypothesis is generated by the hypothesis generator 136 if, after correlating the available pharmaceutical vectors and disease vectors, an anticorrelation is noted between a pharmaceutical vector and a disease vector, i.e. that the pharmaceutical vector displays up-regulation or down-regulation of the same biomolecules the disease vector down-regulates or up-regulates, respectively.

In the preferred embodiment, N hypotheses are generated by the hypothesis generator 136 correlating the pharmaceutical vector representing the pharmaceutical identified by the user computer 110 with one or more disease vectors. This indicates the identified pharmaceutical the pharmaceutical vector represents may be repurposed to treat one or more diseases represented by the disease vectors. In the alternative embodiment, N hypotheses are generated by the hypothesis generator 136 correlating the disease vector representing the disease identified by the user computer 110 with one or more pharmaceutical vectors, indicating the disease could be potentially be treated by the pharmaceutical represented by the pharmaceutical vectors.

Hypothesis confirmation module 137 represents software for determining the strongest one or more hypotheses of the N hypotheses, each hypothesis linking a potential repurposing of the pharmaceutical to treat the diseases. After the hypothesis generator 136 generates the N hypotheses, the hypothesis confirmation module 137 accesses the literature database 170 to obtain biomedical literature (including, by means of non-limiting example, scientific articles, clinical trials, textbooks, and patents) to confirm one or more of the hypotheses. The biomedical literature available in the literature database 170 may be utilized by the repurposing module 130 in mining the literature database 170 to confirm one or more of the N hypotheses, when biomedical literature available via the literature database 170 has previously noticed a connection between the pharmaceutical and the disease. Text mining of the literature database 170 such as via utilization of natural language processing combined with machine learning (based upon previous mining of the literature database 170) is utilized, in an embodiment of the invention, to confirm one or more of the N hypotheses. In an alternative embodiment of the invention, the N hypotheses are ranked by the hypothesis confirmation module 137 according to their strength, based upon text mining the literature database 170 and comparing results of text mining with the N hypotheses.

When text mining the literature database 170, the hypothesis confirmation module 137 may utilize various techniques to better interpret the literature database 170. The hypothesis confirmation module 137 may, when text mining the literature database 170, extract direct relationships from two or more references within the literature database 170. If one reference, for example, indicates a pharmaceutical affects certain biomolecules, and a second reference indicates a disease affects the same certain biomolecules, the literature database 170 may utilize this information to confirm one or more of the N hypotheses, indicating a pharmaceutical may be an appropriate remedy for the disease, confirming one or more of the N hypotheses is strongest. The hypothesis confirmation module 137 may extract indirect relationships from two or more references within the literature database 170. If, for example, one reference indicates a pharmaceutical affects certain biomolecules, and a second reference indicates a disease affects other biomolecules which, in turn, affect the same certain biomolecules, the literature database 170 when text mining references within the literature database 170 may utilize this information to confirm one of the N hypotheses, indicating a pharmaceutical may be an appropriate remedy for the disease, confirming one or more of the N hypotheses is strongest. The hypothesis confirmation module 137 may infer semantic (or text) similarity from two or more references within the literature database 170. If, for example, one reference indicates a certain biomolecule is affected by a pharmaceutical, whereas a second reference indicates a semantically similar biomolecule is affected by a disease, the literature database 170 when text mining within the literature database 170 may utilize this information to confirm one of the N hypotheses. Semantic similarity is determined by the hypothesis confirmation module 137 when words and phrases mentioned around the named biomolecules in biomedical literature available in the literature database 170 are very similar.

Testing module 138 represents software and/or hardware for testing the hypotheses confirmed by the hypothesis confirmation module 137 for real-world efficacy. Hardware associated with testing module 138 may represent hardware to perform automated chemical assays or fluorescence assays to test the hypotheses on cells or tissue samples to determine an efficacy. Testing preferably occurs in the ranked order determined by the hypothesis confirmation module 137, to minimize expenses in repurposing pharmaceuticals, since if a stronger hypothesis is confirmed, it may become unnecessary to test the less highly ranked hypotheses. Testing module 138 may be absent, in embodiments of the invention, with testing of hypotheses performed in a traditional lab setting, including via testing of plasma, skin, hair, nails, bone marrow, etc., followed by later-stage clinical testing of hypotheses.

In the exemplary embodiment, pharmaceutical database 150 includes pharmaceutical omics database 155.

Pharmaceutical omics database 155 represents hardware and/or software for storing pharmaceutical expression signatures indicating which biomolecules are up-regulated and which are down-regulated by each pharmaceutical. Multiple pharmaceutical expression signatures regarding multiple pharmaceuticals are stored by the pharmaceutical omics database 155, and are transmitted to the pharmaceutical vector module 133 upon request. Pharmaceutical expression signatures stored in pharmaceutical omics database 155 are generated from lab-testing of pharmaceuticals, such as via a microarray, and may be made available from a public repository (such as Cmap), proprietary libraries maintained by a pharmaceutical company, internal experiments utilizing various technologies, etc. The pharmaceutical expression signatures stored in pharmaceutical omics database 155 may be continuously updated as discoveries continue to be made by medical professionals and are uploaded to pharmaceutical omics database 155, published in biomedical literature, or made publicly available in another way. Pharmaceutical expression signatures stored within the pharmaceutical omics database 155 are further utilized as discussed herein.

In the exemplary embodiment, disease database 160 includes disease omics database 165.

Disease omics database 165 represents hardware and/or software for storing disease expression signature indicating which biomolecules are up-regulated and which are down-regulated by a disease. Multiple disease expression signatures regarding multiple diseases are stored by the disease omics database 165, and are transmitted to the disease vector module 135 upon request. Disease expression signatures stored in disease omics database 165 are generated from lab-testing of diseases, such as via a microarray, and may be made available from a public library (such as Gene Expression Omnibus for Diseases), proprietary library, internal experiments utilizing various technologies, etc. The disease expression signatures stored in the disease omics database 165 may be continuously updated as discoveries continue to be made by medical professionals and are uploaded to the disease omics database 165, published in biomedical literature, or made publicly available in another way. Disease expression signatures stored within the disease omics database 165 are further utilized as discussed herein.

In the exemplary embodiment, literature database 170 includes biomedical literature database 175.

Biomedical literature database 175 represents hardware and/or software for storing biomedical literature of various sorts, including journal articles, scientific articles, news articles, magazine articles, textbooks, patents, symposium proceedings, clinical studies, medical manuals, and any other sort of written text discussing pharmaceuticals and diseases which may be utilized within the presently disclosed invention. All of the biomedical literature available in the biomedical literature database 175 is continuously updated as new articles are published or made publicly available. All of the biomedical literature available in biomedical literature database 175 is digital in original form, or has been optical-character recognized for text mining and other uses within the presently disclosed invention. As discussed elsewhere herein, biomedical literature may have data regarding a pharmaceutical or diseases which may be directly, indirectly, or semantically inferred to confirm hypotheses, as further discussed herein.

Figure 2:
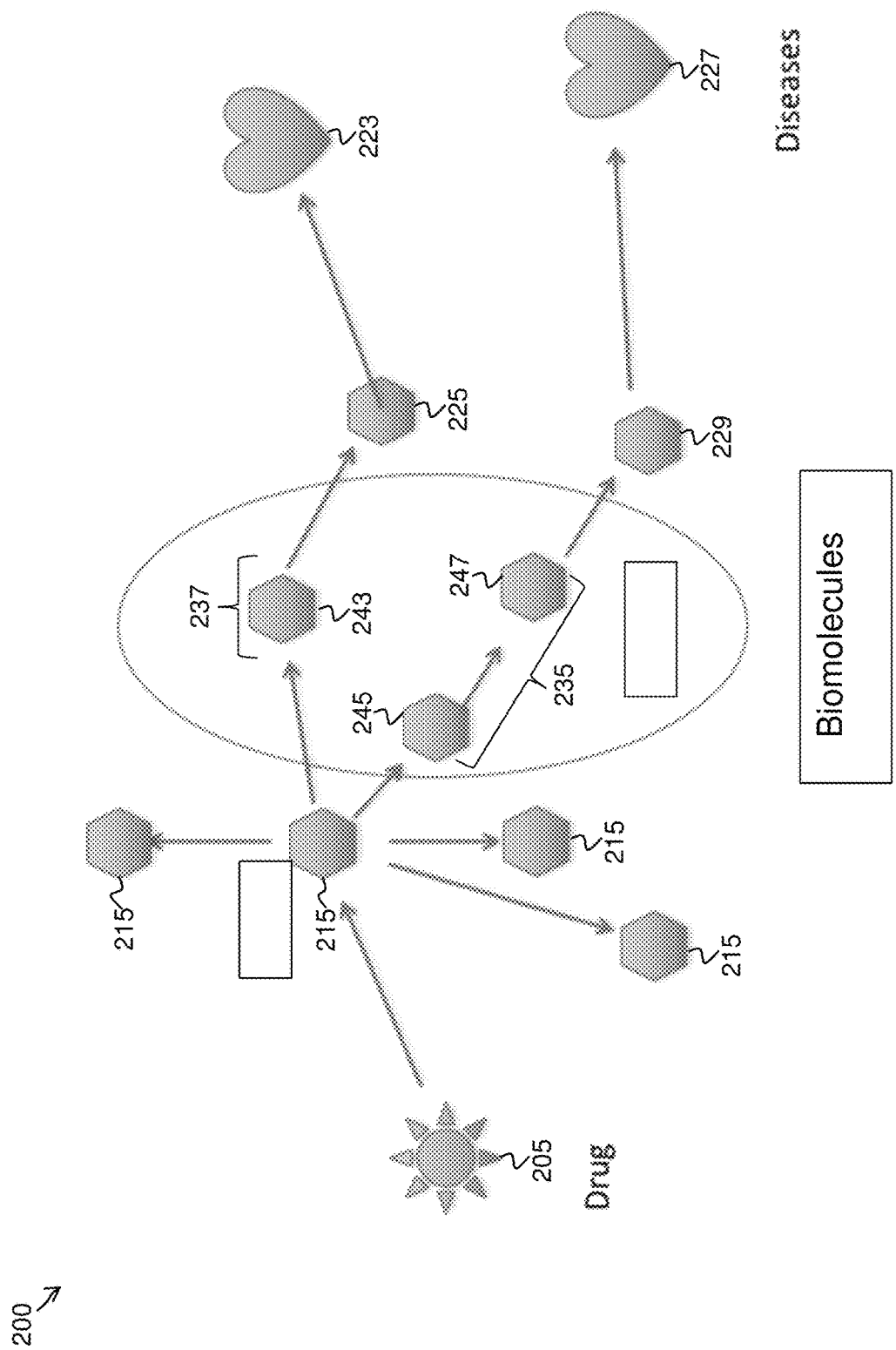
FIG. 2 is a directed graph model illustrating steps in accelerated pharmaceutical repurposing using omics data and literature text mining, in accordance with an embodiment of the invention.

FIG. 2 is a directed graph model 200 illustrating steps in accelerated pharmaceutical repurposing using omics data and literature text mining by the repurposing module 130 in conjunction with the user computer 110, pharmaceutical database 150, disease database 160, and literature database 170, in accordance with an embodiment of the invention. As displayed within FIG. 2, after the communication module 131 receives an identification of a pharmaceutical for repurposing study, the identified pharmaceutical becomes source 205 for the directed graph model 200 pictured in FIG. 2. The pharmaceutical vector module 133 retrieves from the pharmaceutical omics database 155 of pharmaceutical database 150 a pharmaceutical expression signature for the pharmaceutical. The differential expressions of biomolecules affected by the pharmaceutical are utilized by the pharmaceutical vector module 133 to generate pharmaceutical vectors, represented in FIG. 2 as nodes 215. The disease vector module 135 retrieves from the disease omics database 165 of disease database 160 a plurality of disease expression signatures which are utilized by the disease vector module 135 to generate disease vectors, represented in FIG. 2 as 225 and 229. The disease associated with each disease vector 225, 229 is displayed in FIG. 2 as 223 and 227. Diseases 223 and 227, are in effect, sinks in the directed graph model 200 displayed in FIG. 2. Although only two diseases 223, 227 are displayed in FIG. 2 for ease of understanding, the presently disclosed invention contemplates the disease vector module 135 generating dozens or more of disease vectors for dozens or more of diseases, to generate the strongest one or more hypotheses. The hypothesis generator 136 then generates N hypotheses correlating one of the pharmaceutical vectors 215 and the disease vectors 225, 229. The two hypotheses generated by hypothesis generator 136 are represented in FIG. 2 as group of nodes 235 and node 237. Each node 243, 245, 247 in the hypotheses 235, 237 represents a biomolecule up-regulated or down-regulated by drug 205, and, correspondingly, down-regulated or up-regulated by diseases 223, 227. Hypothesis confirmation module 137 determines which of the two hypotheses 235, 237 is strongest (in the example displayed in FIG. 2), via utilization of text mining, as further discussed herein. In confirming one of the hypotheses 235, 237, hypothesis confirmation module 137 may perform a graph traversal of directed graph model 200 utilizing a graph label propagation algorithm or another graph traversal algorithm, with each node 243, 245, 247 in the hypotheses 235, 237 accorded a weight, and all weights in the graph traversal summed or multiplied, with the highest total for hypotheses 235, 237 determined by the hypothesis confirmation module 137 to be the strongest hypothesis.

FIGS. 3A, 3B, 3C, and 3D are process flow diagrams illustrating various operational steps in accelerated pharmaceutical repurposing using omics data and literature text mining by the hypothesis generator 136 and hypothesis confirmation module 137, in accordance with an embodiment of the invention. At FIG. 3A, displayed is a pharmaceutical vector 310 and a disease vector 315, after both vectors are generated as discussed herein or obtained in an alternative manner. The pharmaceutical vector 310 indicates as displayed that biomolecule G1 is differentially expressed by pharmaceutical 0.43 from normal, biomolecule G2 is differentially expressed by pharmaceutical 2.56 from normal, and biomolecule G3 is differentially expressed by pharmaceutical 3.67 from normal. Disease vector 315 indicates as displayed that biomolecule G1 is differentially expressed by disease 1.76 from normal, biomolecule G2 is differentially expressed by disease 0.45 from normal, and biomolecule G3 is differentially expressed by disease −3.52 from normal. Hypothesis generator 136 may correlate pharmaceutical vector 310 and disease vector 315 to generate one of the N hypotheses by confirming an anticorrelation between each of biomolecule G1, G2, and G3 within vectors 310 and 315, specifically because pharmaceutical vector 310 down-regulates G1 and up-regulates G2 and G3, whereas disease vector 315 up-regulates G1 and down-regulates G2 and G3. Thus, an anticorrelation is noted between pharmaceutical vector 310 and disease vector 315, and therefore the associated pharmaceutical and diseases, and the hypothesis generator 136 generates one of the N hypotheses, for further use as discussed.

Figure 3A:
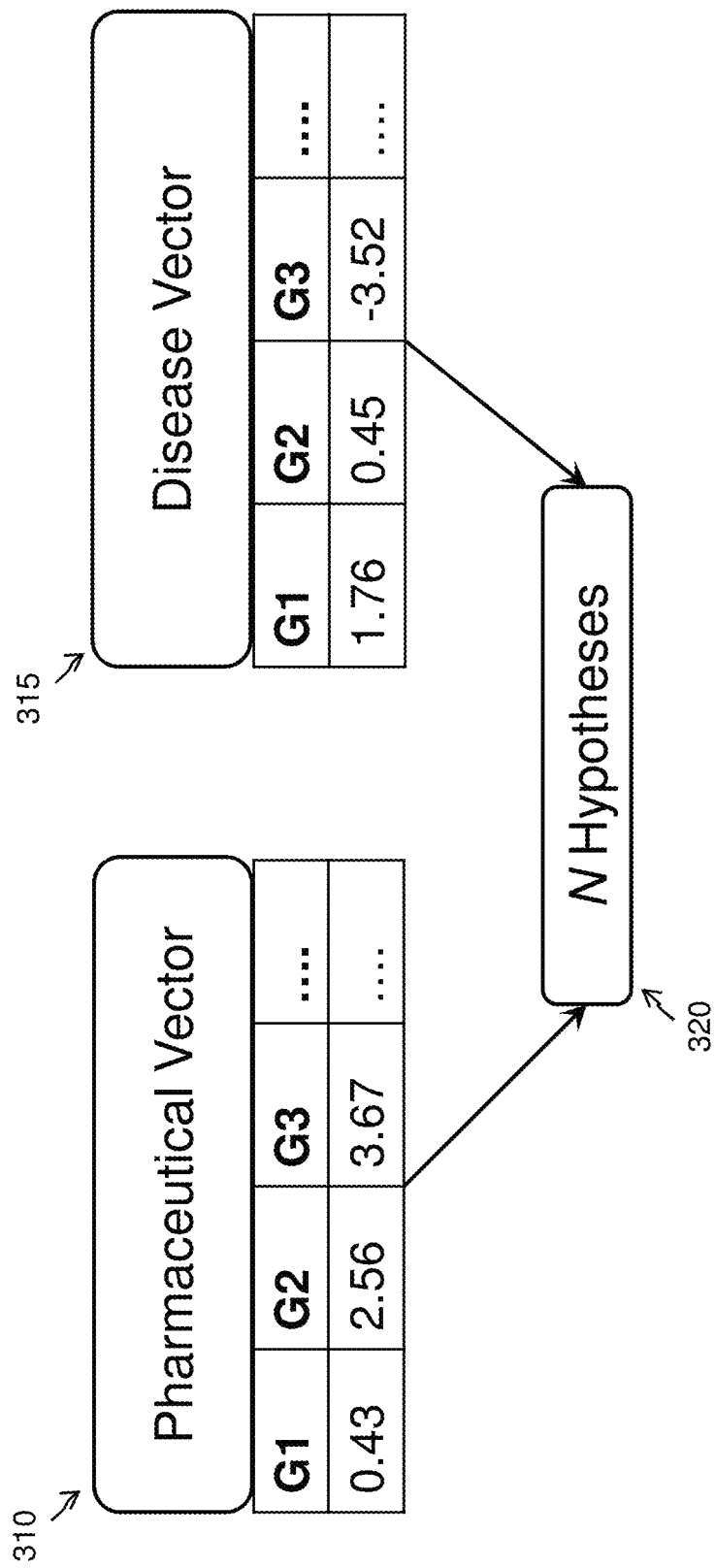
FIGS. 3A, 3B, 3C, and 3D are process flow diagrams illustrating various operational steps in accelerated pharmaceutical repurposing using omics data and literature text mining, in accordance with an embodiment of the invention.
Figure 3B:
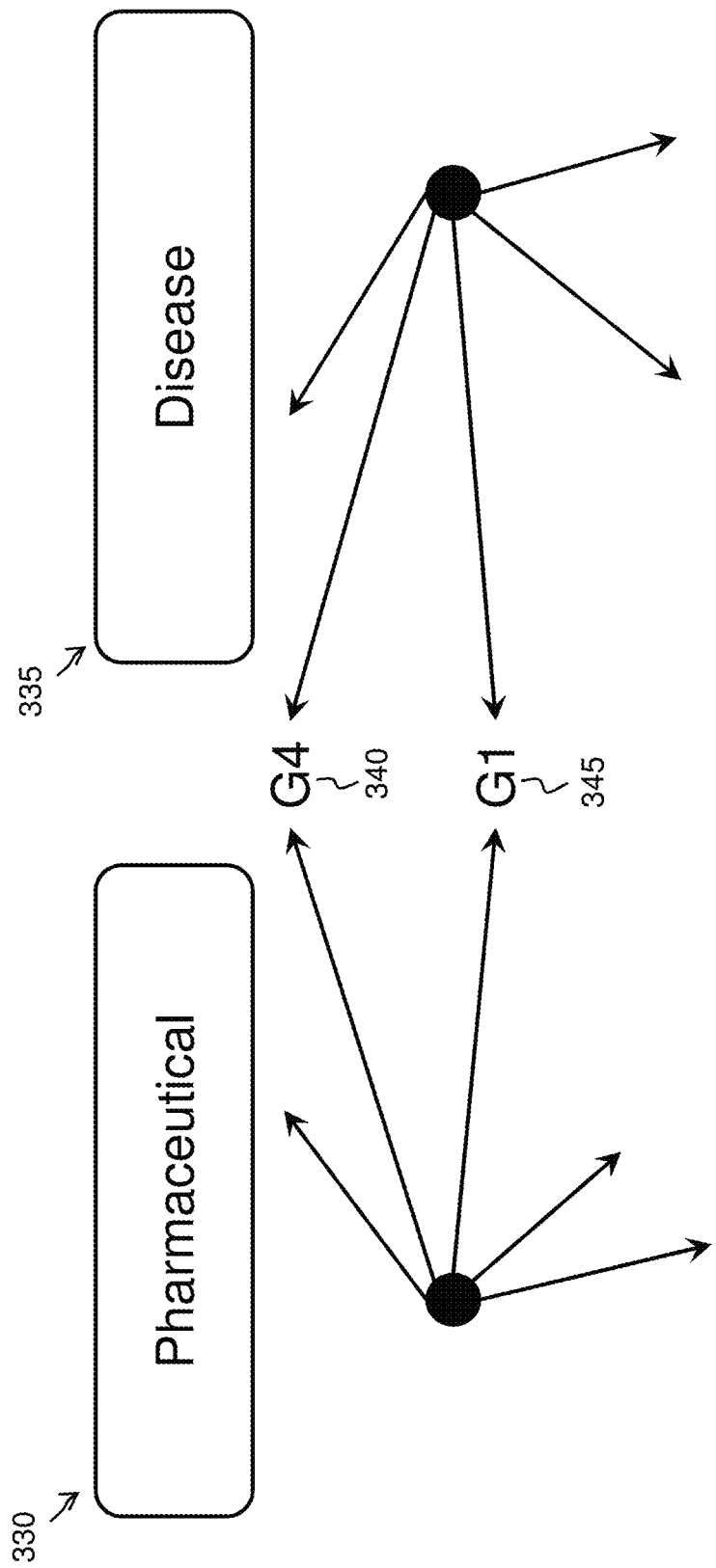

FIG. 3B displays results of text mining by the hypothesis confirmation module 137 a literature database 170 to extract direct relationships. Two references are mined by the hypothesis confirmation module 137, one regarding a pharmaceutical 330 and one regarding a disease 335. After text mining, noted is that biomolecule G4 340 and biomolecule G1 345 are referred to directly by the pharmaceutical reference 330 and the disease reference 335. In these circumstances, the hypothesis confirmation module 137 may confirm one of the N hypotheses which indicated a potential repurposing for the pharmaceutical to treat the disease.

Figure 3C:
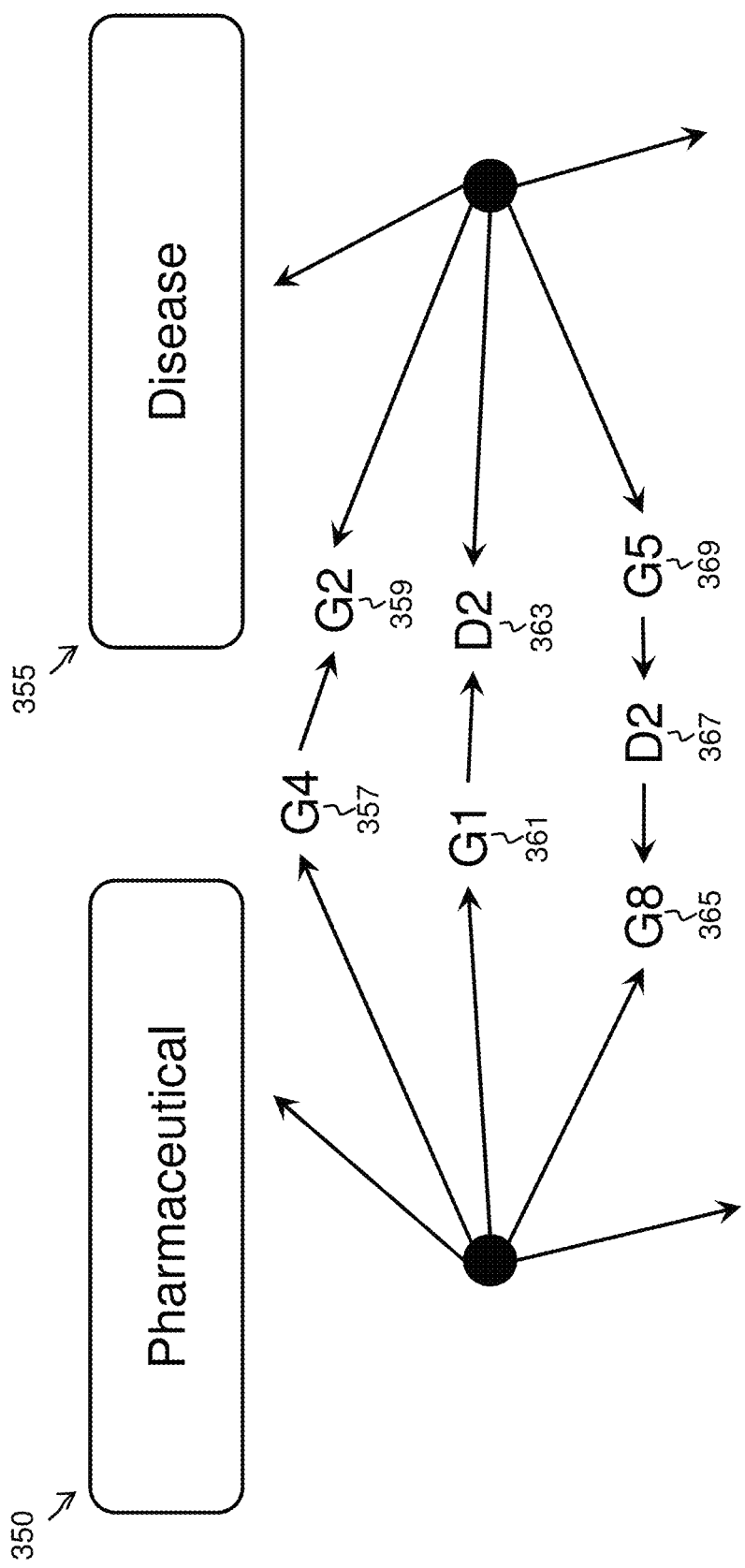

FIG. 3C displays results of text mining a literature database 170 to extract indirect relationships by the hypothesis confirmation module 137. Again, two references are mined, one regarding a pharmaceutical 350 and one regarding a disease 355. After text mining by the hypothesis confirmation module 137, noted is that biomolecule G4 357 and biomolecule G2 359 are indirectly related (represented as nodes 357, 359). Noted also is that biomolecule G1 361 and biomolecule D2 363 are indirectly related (represented as nodes 361, 363). Finally, note that biomolecules G8 365, D2 367, and G5 369 are indirectly related (represented as nodes 365, 367, 369). Any or all of these indirect connections may confirm one or more of the N hypotheses which notes an anticorrelation between each of these indirect relationships. In an embodiment of the invention, hypothesis confirmation module 137 determines which indirect relationship(s) are strongest by determining the smallest number of nodes connecting pharmaceutical 350 and disease 355. With regard to FIG. 3C, path of biomolecule G4 357 and biomolecule G2 359 has two nodes between pharmaceutical 350 and disease 355. Path of biomolecule G1 361 and biomolecule D2 363 also has two nodes between pharmaceutical 350 and disease 355. Path of biomolecule G8 365, biomolecule D2 367, and biomolecule G5 369 has three nodes between pharmaceutical 350 and disease 355. The hypothesis confirmation module 137 thus determines that the two steps between biomolecule G4 357 and biomolecule G2 359, as well as the two steps between biomolecule G1 361 and biomolecule D2 363 are the shortest number of steps between pharmaceutical 350 and disease 355 and are thus the most likely to support the strongest one or more hypotheses of the N hypotheses. In alternative embodiments, various weights are placed upon every node 357-369, and all weights along a path of nodes summed or multiplied to determine an indirect relationship score for each path of nodes 357-369, with the path with the highest summed or multiplied weight used to confirm the strongest one or more hypotheses of the N hypotheses.

Figure 3D:
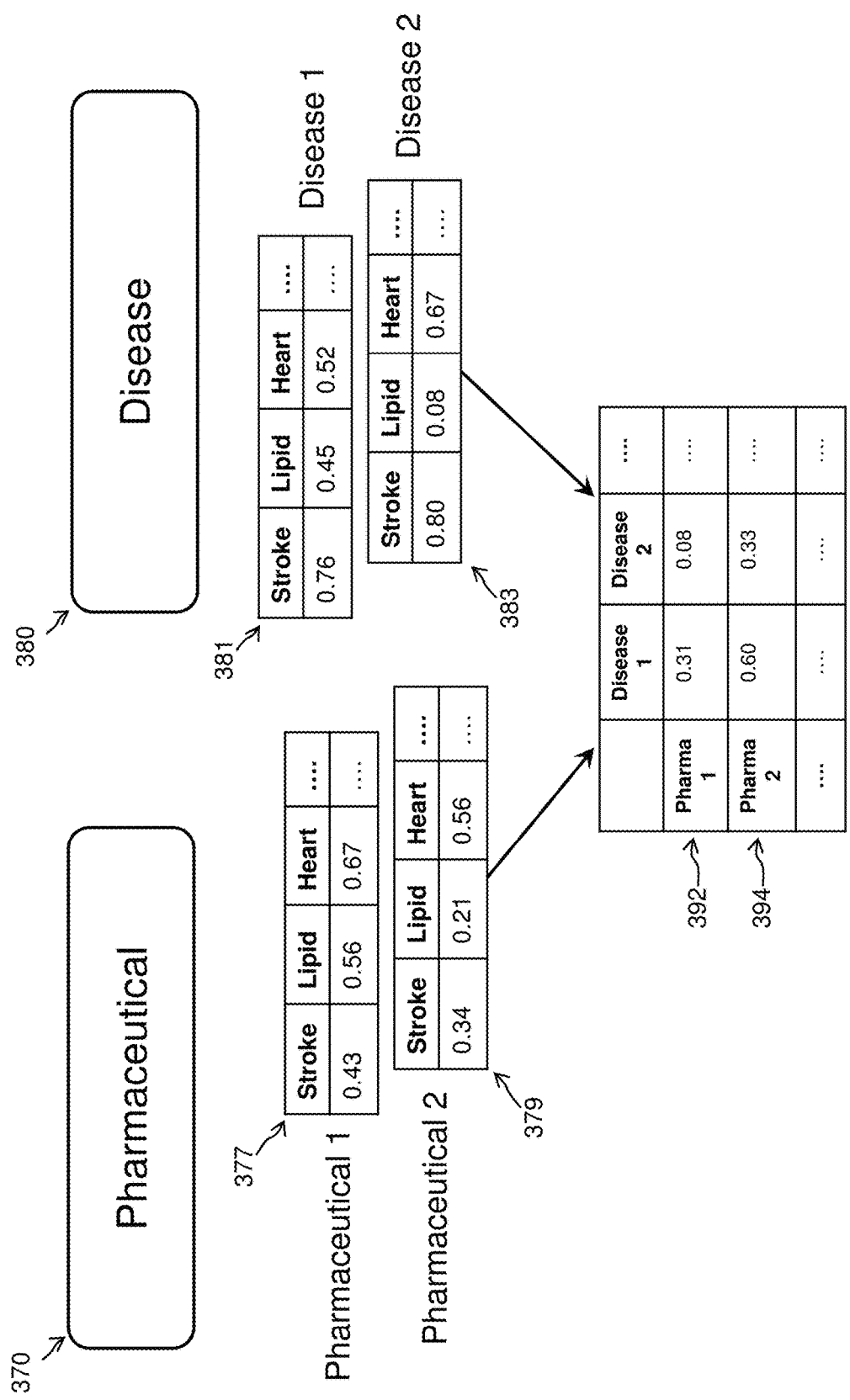

FIG. 3D displays results of text mining by the hypothesis confirmation module 137 of literature database 170 to infer semantic similarity between references in seeking to confirm one of the N hypotheses. Two references are considered, one pharmaceutical reference regarding multiple pharmaceuticals 370 and one disease reference regarding multiple diseases 380. Within the pharmaceutical reference 370, after text analysis by the hypothesis confirmation module 137, Pharmaceutical 1 377 is discussed in the pharmaceutical reference 370, and the term "stroke" has a relevance of 0.43, the term "lipid" has a relevance of 0.56, and the term "heart" has a relevance of 0.67. Pharmaceutical 2 379 is also discussed in the pharmaceutical reference 370, and the term "stroke" has a relevance of 0.34, the term "lipid" has a 0.21 relevance, and the term "heart" has a 0.56 relevance. Within the disease reference 380, after text analysis by the hypothesis conformation module 137, disease 1 381 is discussed in the disease reference 380, and the term "stroke" has a relevance of 0.76, the term "lipid" has a 0.45 relevance, and the term "heart" has a 0.52 relevance. Disease 2 383 is discussed in the disease reference 380, and the term "stroke" has a relevance of 0.80, the term "lipid" has a 0.08 relevance, and the term "heart" has a 0.67 connection. The hypothesis confirmation module 137, after inferring semantic similarity between the pharmaceutical reference 370 and the disease reference 380, notes a 0.31 correlation between pharmaceutical 1 and disease 1, as displayed 392, and a 0.08 correlation between pharmaceutical 1 and disease 2, also as displayed 392, indicating that pharmaceutical 1 is more likely to be repurposed to be a treatment for disease 1. As displayed 394, the hypothesis confirmation module 137 notes a 0.60 correlation between pharmaceutical 2 and disease 1, and a 0.33 correlation between pharmaceutical 2 and disease 2, also as displayed 394, indicating that pharmaceutical 2 is more likely to be repurposed a treatment for disease 1, confirming one of the N hypotheses. In an embodiment of the invention, the hypothesis confirmation module 137 may determine a semantic similarity score between terminology utilized in pharmaceutical reference 370 and disease reference 380. If pharmaceutical reference 370 and disease reference 380 share a large number of relevant terms, a high semantic similarity score might be calculated, while if pharmaceutical reference 370 and disease reference 380 do not share a large number of relevant terms, a low semantic similarity score may be calculated. The hypothesis confirmation module 137 may multiply each correlation 392, 394 by the semantic similarity score, for better results in confirming one of the N hypotheses.

Figure 4A:
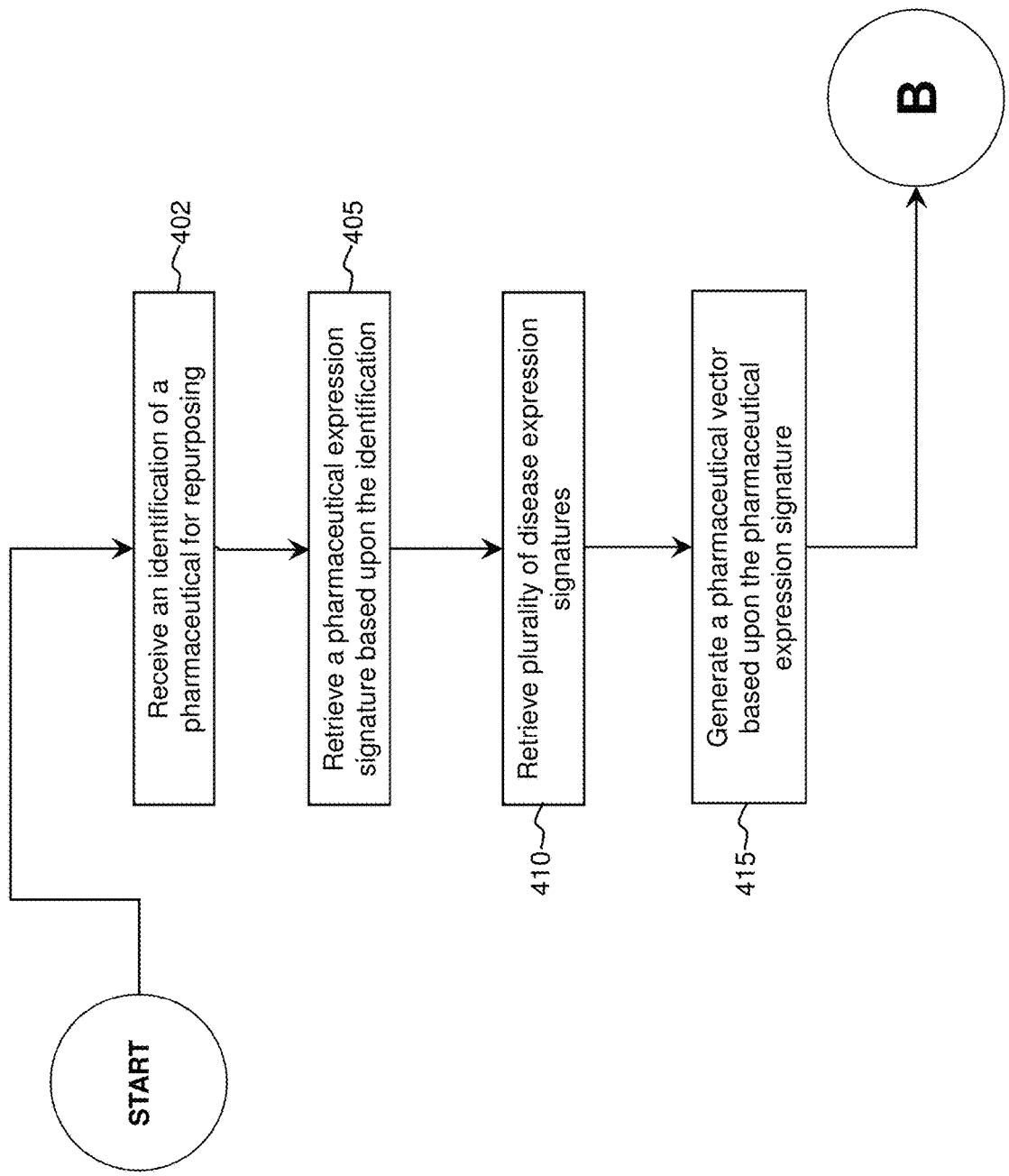
FIGS. 4A and 4B are a flowchart depicting operational steps that a hardware component, multiple hardware components, and/or a hardware appliance may execute, in accordance with an embodiment of the invention.
Figure 4B:
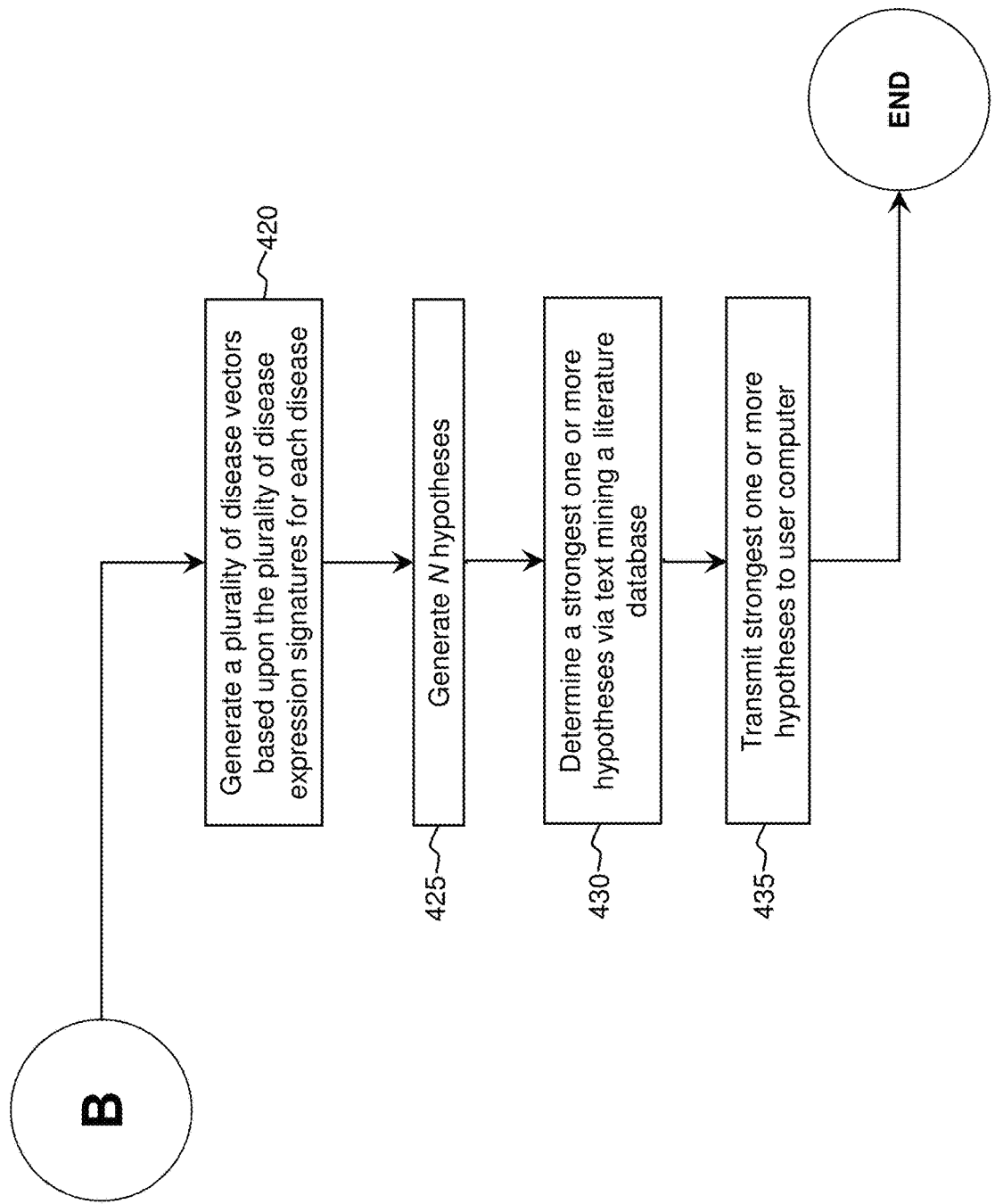

FIGS. 4A and 4B are a flowchart depicting operational steps that a hardware component, multiple hardware components, and/or a hardware appliance may execute, in accordance with an embodiment of the invention. As execution begins in FIG. 4A, at step 402, the communication module 131 of repurposing module 130 receives an identification of a pharmaceutical from the user computer 110 for repurposing. At step 405, the pharmaceutical vector module 133 of the repurposing module 130 retrieves from the pharmaceutical database 150 a pharmaceutical expression signature based upon the identification. The pharmaceutical expression signature indicates differential expressions of a plurality of biomolecules regulated by the pharmaceutical versus a control. At step 410, the disease vector module 135 of the repurposing module 130 retrieves a plurality of disease expression signatures from a disease database 160, each disease expression signature indicating differential expressions of a plurality of biomolecules affected by a disease versus a control. At step 415, the pharmaceutical vector module 133 of repurposing module 130 generates a pharmaceutical vector based upon the pharmaceutical expression signature for the pharmaceutical.

Continuing in FIG. 4B, at step 420, the disease vector module 135 of repurposing module 130 generates a plurality of disease vectors based upon the plurality of disease expression signatures for each disease. At step 425, the hypothesis generator 136 of repurposing module 130 generates N hypotheses correlating the pharmaceutical vector and one or more of the plurality of disease vectors, each of the N hypotheses indicating an anticorrelation between the pharmaceutical expression signature and one or more disease expression signatures of the plurality of disease expression signatures. Each hypothesis indicates a potential repurposing for the pharmaceutical to treat the disease. At step 430, the hypothesis confirmation module 137 of repurposing module 130 determines a strongest one or more hypotheses by text mining the literature database 170 and comparing results of the text mining with the N hypotheses. The hypothesis confirmation module 137 may further rank the N hypotheses according to each of their strengths. At step 435, the communication module 131 of repurposing module 130 transmits the strongest one or more hypotheses (or the N hypotheses according to strength) to the user computer 110.

Figure 5:
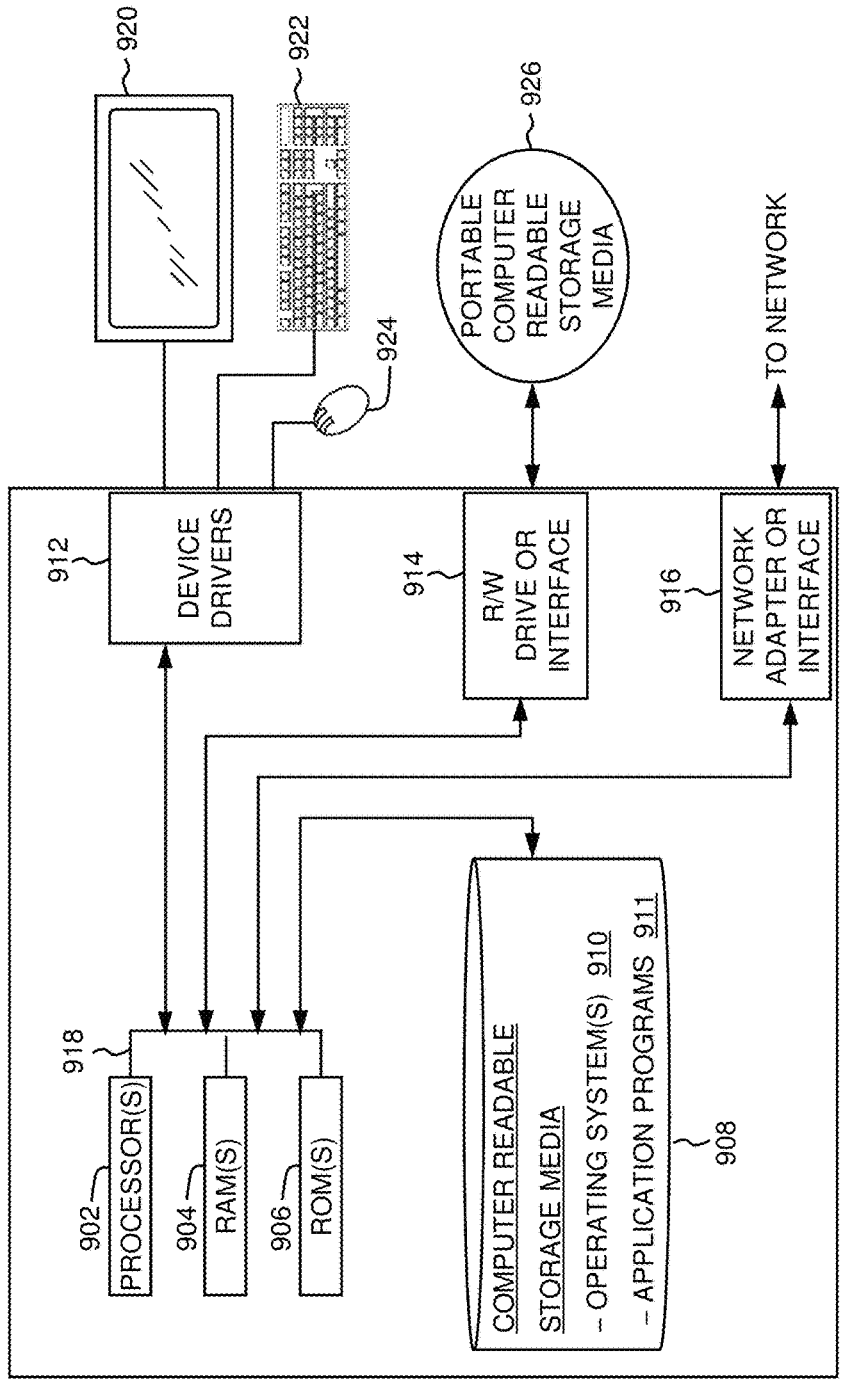
FIG. 5 depicts a block diagram of components of user computer, repurposing module, pharmaceutical database, literature database, and disease database of FIG. 1, in accordance with an embodiment of the present invention.

FIG. 5 depicts a block diagram of components of user computer 110, repurposing module 130, pharmaceutical database 150, disease database 160, and literature database 170 in the environment 100 for accelerated pharmaceutical repurposing utilizing omics data and literature text mining, in accordance with an embodiment of the present invention. It should be appreciated that FIG. 5 provides only an illustration of one implementation and does not imply any limitations with regard to the environments in which different embodiments may be implemented. Many modifications to the depicted environment may be made.

User computer 110, repurposing module 130, pharmaceutical database 150, disease database 160, and literature database 170 may include one or more processors 902, one or more computer-readable RAMs 904, one or more computer-readable ROMs 906, one or more computer readable storage media 908, device drivers 912, read/write drive or interface 914, network adapter or interface 916, all interconnected over a communications fabric 918. Communications fabric 918 may be implemented with any architecture designed for passing data and/or control information between processors (such as microprocessors, communications and network processors, etc.), system memory, peripheral devices, and any other hardware components within a system.

One or more operating systems 910, and one or more application programs 911, for example, environment 100 for accelerated pharmaceutical repurposing utilizing omics data and literature text mining, are stored on one or more of the computer readable storage media 908 for execution by one or more of the processors 902 via one or more of the respective RAMs 904 (which typically include cache memory). In the illustrated embodiment, each of the computer readable storage media 908 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

User computer 110, repurposing module 130, pharmaceutical database 150, disease database 160, and literature database 170 may also include a R/W drive or interface 914 to read from and write to one or more portable computer readable storage media 926. Application programs 911 on user computer 110, repurposing module 130, pharmaceutical database 150, disease database 160, and literature database 170 may be stored on one or more of the portable computer readable storage media 926, read via the respective R/W drive or interface 914 and loaded into the respective computer readable storage media 908.

User computer 110, repurposing module 130, pharmaceutical database 150, disease database 160, and literature database 170 may also include a network adapter or interface 916, such as a TCP/IP adapter card or wireless communication adapter (such as a 4G wireless communication adapter using OFDMA technology). Application programs 911 on user computer 110, repurposing module 130, pharmaceutical database 150, disease database 160, and literature database 170 may be downloaded to the computing device from an external computer or external storage device via a network (for example, the Internet, a local area network or other wide area network or wireless network) and network adapter or interface 916. From the network adapter or interface 916, the programs may be loaded onto computer readable storage media 908. The network may comprise copper wires, optical fibers, wireless transmission, routers, firewalls, switches, gateway computers and/or edge servers.

User computer 110, repurposing module 130, pharmaceutical database 150, disease database 160, and literature database 170 may also include a display screen 920, a keyboard or keypad 922, and a computer mouse or touchpad 924. Device drivers 912 interface to display screen 920 for imaging, to keyboard or keypad 922, to computer mouse or touchpad 924, and/or to display screen 920 for pressure sensing of alphanumeric character entry and user selections. The device drivers 912, R/W drive or interface 914 and network adapter or interface 916 may comprise hardware and software (stored on computer readable storage media 908 and/or ROM 906).

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a method, computer program product, and/or computer system at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, computer program products, and apparatus (systems) according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of method, system, and computer program product according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 6:
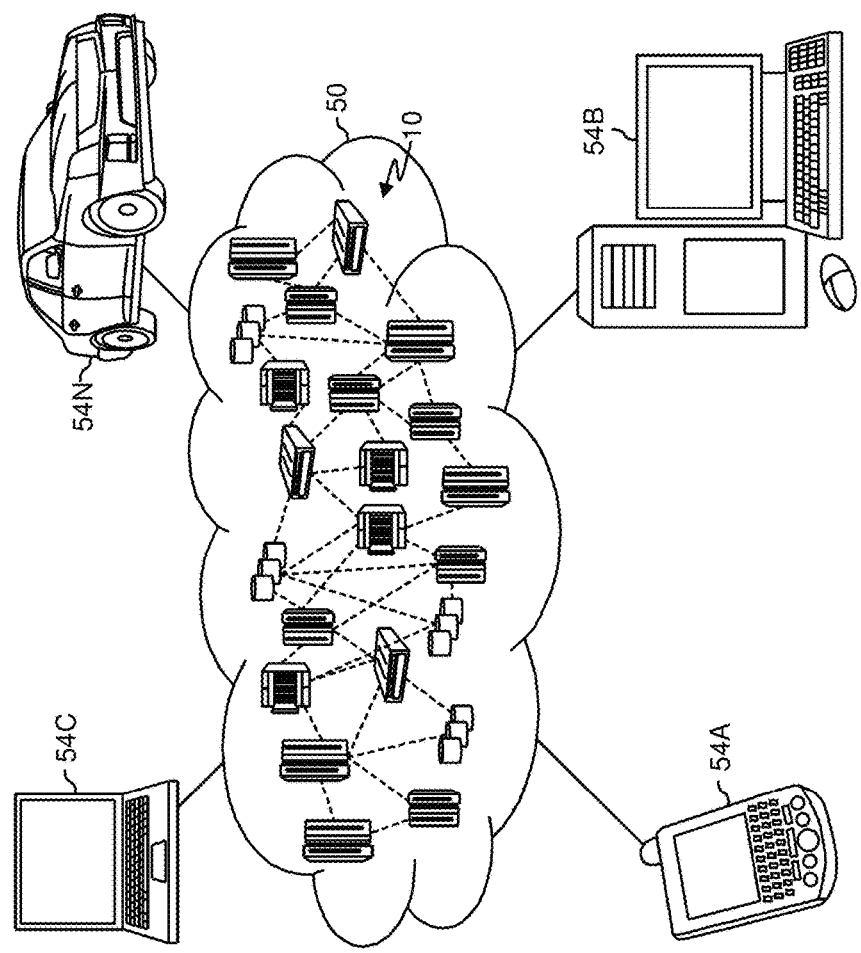
FIG. 6 depicts a cloud computing environment, in accordance with an embodiment of the present invention.

Referring now to FIG. 6, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that computing nodes 10 and cloud computing environment 50 can communicate with any type of computerized device over any type of network and/or network addressable connection (e.g., using a web browser).

Figure 7:
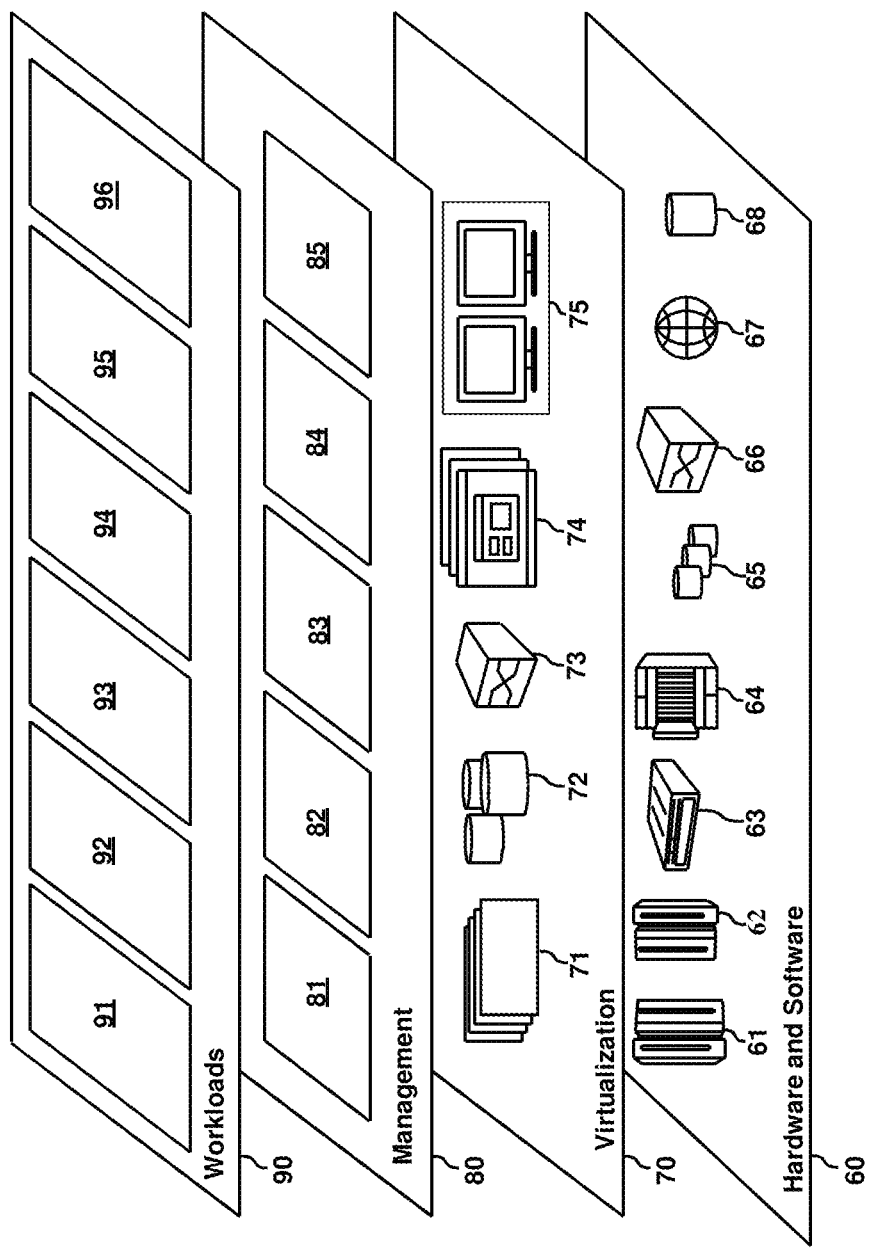
FIG. 7 depicts abstraction model layers, in accordance with an embodiment of the present invention.

Referring now to FIG. 7, a set of functional abstraction layers provided by cloud computing environment 50 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and the environment 100 for accelerated pharmaceutical repurposing utilizing omics data and literature text mining.

Based on the foregoing, a method, system, and computer program product have been disclosed. However, numerous modifications and substitutions can be made without deviating from the scope of the present invention. Therefore, the present invention has been disclosed by way of example and not limitation.

What is claimed is:

1. A method comprising:
receiving by a computing device an identification of a pharmaceutical;
retrieving, by the computing device, a pharmaceutical expression signature for the pharmaceutical, the pharmaceutical expression signature indicating differential expressions of biomolecules regulated by the pharmaceutical versus a first control;
retrieving, by the computing device, disease expression signatures from a disease omics database, each disease expression signature indicating a differential expression of at least one biomolecule affected by a respective disease versus a second control;
generating by the computing device a pharmaceutical vector based upon the pharmaceutical expression signature;
generating, by the computing device, disease vectors based upon the disease expression signatures, respectively;
identifying, by the computing device:
a first anticorrelation between the pharmaceutical vector and one of the disease vectors, the first anticorrelation indicating a first potential repurposing for the pharmaceutical to treat a first disease, the first disease corresponding to the one of the disease vectors; and
a second anticorrelation between the pharmaceutical vector and another one of the disease vectors, the second anticorrelation indicating a second potential repurposing for the pharmaceutical to treat a second disease, the second disease corresponding to the other one of the disease vectors;
text mining, by the computing device, a literature database to rank the first and second anticorrelations and the first and second potential repurposings, wherein the text mining comprises identifying references from the literature database, and wherein the text mining comprises:
extracting from the references a first indication of a direct pharmaceutical effect on a first biomolecule via the pharmaceutical and on the first biomolecule via at least one of the first and second diseases, and extracting from the references:
a second indication of an indirect of pharmaceutical effect on a second biomolecule via at least one of the pharmaceutical and the first and second diseases and
a third indication of a pharmaceutical effect on the second biomolecule via another of the pharmaceutical and the first and second diseases;
generating, by the computing device, a first confirmation score for the first potential repurposing and a second confirmation score for the second potential repurposing, wherein the first confirmation score and the second confirmation score are based on the text mining;
presenting, via the computing device, a ranking of the first confirmation score and the second confirmation score; and
testing, via at least one test selected from the group consisting of a chemical assay and a fluorescence assay, the first potential repurposing or the second potential repurposing according to which of the first and the second potential repurposing corresponds to a higher ranking of the first confirmation score and the second confirmation score.

2. The method of claim 1, wherein the text mining of the literature database uses machine learning and natural language processing.

3. The method of claim 1, wherein each biomolecule is a gene, a protein, or a metabolite.

4. The method of claim 1, wherein the differential expressions of the biomolecules regulated by the pharmaceutical and the differential expressions of the biomolecules affected by the diseases indicate one or more biomolecules up-regulated and one or more biomolecules down-regulated with respect to the first control or the second control.

5. The method of claim 1, wherein the text mining further comprises inferring, from the references, a semantic similarity between the references.

6. The method of claim 5, wherein the semantic similarity is between a name of a third biomolecule affected by the pharmaceutical and a name of a fourth biomolecule affected by at least one of the first and second diseases, and wherein the names are from the references.

7. The method of claim 5, wherein the semantic similarity is between a first word associated with a third biomolecule affected by the pharmaceutical and a second word associated with a fourth biomolecule affected by at least one of the first and second diseases, and wherein the first word and the second word are from the references.

8. A computer program product comprising:
one or more non-transitory computer-readable storage media and program instructions stored on the one or more non-transitory computer-readable storage media, wherein the program instructions are configured to cause, when executed by a computing device, the computing device to perform a method comprising:
receiving an identification of a pharmaceutical;
retrieving a pharmaceutical expression signature for the pharmaceutical, the pharmaceutical expression signature indicating differential expressions of biomolecules regulated by the pharmaceutical versus a first control;
retrieving disease expression signatures from a disease omics database, each disease expression signature indicating a differential expression of at least one biomolecule affected by a respective disease versus a second control;
generating a pharmaceutical vector based upon the pharmaceutical expression signature;

generating disease vectors based upon the disease expression signatures, respectively;
identifying:
a first anticorrelation between the pharmaceutical vector and one of the disease vectors, the first anticorrelation indicating a first potential repurposing for the pharmaceutical to treat a first disease, the first disease corresponding to the one of the disease vectors; and
a second anticorrelation between the pharmaceutical vector and another one of the disease vectors, the second anticorrelation indication a second potential repurposing for the pharmaceutical to treat a second disease, the second disease corresponding to the other one of the disease vectors;
text mining a literature database to rank the first and second anticorrelations and the first and second potential repurposings, wherein the text mining comprises identifying references from the literature database, and wherein the text mining comprises:
extracting from the references a first indication of a direct pharmaceutical effect on a first biomolecule via the pharmaceutical and on the first biomolecule via the first and second diseases, and
extracting from the references:
a second indication of an indirect of pharmaceutical effect on a second biomolecule via at least one of the pharmaceutical and the first and second diseases, and
a third indication of a pharmaceutical effect on the second biomolecule via another of the pharmaceutical and the first and second diseases
generating a first confirmation score for the first potential repurposing and a second confirmation score for the second potential repurposing, wherein the first confirmation score and the second confirmation score are based on the text mining;
presenting a ranking of the first confirmation score and the second confirmation score; and
testing, via at least one test selected from the group consisting of a chemical assay and a fluorescence assay, the first potential repurposing or the second potential repurposing according to which of the first and the second potential repurposing corresponds to a higher ranking of the first confirmation score and the second confirmation score.

9. The computer program product of claim 8, wherein the text mining of the literature database uses machine learning and natural language processing.

10. The computer program product of claim 8, wherein each biomolecule is a gene, a protein, or a metabolite.

11. The computer program product of claim 8, wherein the differential expressions of the biomolecules regulated by the pharmaceutical and the differential expressions of the biomolecules affected by the diseases indicate one or more biomolecules up-regulated and one or more biomolecules down-regulated with respect to the first control or the second control.

12. The computer program product of claim 8, wherein the text mining further comprises inferring, from the references, a semantic similarity between the references.

13. The computer program product of claim 12, wherein the semantic similarity is between a name of a third biomolecule affected by the pharmaceutical and a name of a fourth biomolecule affected by at least one of the first and second diseases, and wherein the names are from the references.

14. The computer program product of claim 12, wherein the semantic similarity is between a first word associated with a third biomolecule affected by the pharmaceutical and a second word associated with a fourth biomolecule affected by at least one of the first and second diseases, and wherein the first word and the second word are from the references.

15. A computer system comprising:
one or more computer processors;
one or more computer-readable storage media; and
program instructions stored on the computer-readable storage media and configured to cause the computer system to perform a method comprising:
receiving an identification of a pharmaceutical;
retrieving a pharmaceutical expression signature for the pharmaceutical, the pharmaceutical expression signature indicating differential expressions of biomolecules regulated by the pharmaceutical versus a first control;
retrieving disease expression signatures from a disease omics database, each disease expression signature indicating a differential expression of at least one biomolecule affected by a respective disease versus a second control;
generating a pharmaceutical vector based upon the pharmaceutical expression signature;
generating disease vectors based upon the disease expression signatures, respectively;
identifying:
a first anticorrelation between the pharmaceutical and one of the disease vectors, the first anticorrelation indicating a first potential repurposing for the pharmaceutical to treat a first disease, the first disease corresponding to the one of the disease vectors; and
a second anticorrelation between another one of the pharmaceutical vectors and another one of the disease vectors, the second anticorrelation indicating a second potential repurposing for the pharmaceutical to treat a second disease, the second disease corresponding to the other one of the disease vectors;
text mining a literature database to rank the first and second anticorrelations and the first and second potential repurposings, wherein the text mining comprises identifying references from the literature database, and wherein the text mining comprises:
extracting from the references a first indication of a direct pharmaceutical effect on a first biomolecule via the pharmaceutical and on the first biomolecule via at least one of the first and second diseases, and
extracting from the references:
a second indication of an indirect pharmaceutical effect on a second biomolecule via at least one of the pharmaceutical and the first and second diseases, and
a third indication of a pharmaceutical effect on the second biomolecule via another of the pharmaceutical and the first and second diseases
generating a first confirmation score for the first potential repurposing and a second confirmation score for the second potential repurposing, wherein the first confirmation score and the second confirmation score are based on the text mining;
presenting a ranking of the first confirmation score and the second confirmation score; and testing, via at least one test selected from the group consisting of a chemical assay and a fluorescence assay, the first potential repurposing or the second potential repurposing according to which of the first and the second potential repurposing corresponds to a higher ranking of the first confirmation score and the second confirmation score.

16. The computer system of claim 15, wherein the text mining of the literature database uses machine learning and natural language processing.

17. The computer system of claim 15, wherein each biomolecule is a gene, a protein, or a metabolite.

18. The computer system of claim 15, wherein the differential expressions of the biomolecules regulated by the pharmaceutical and the differential expressions of the biomolecules affected by the diseases indicate one or more biomolecules up-regulated and one or more biomolecules down-regulated.

19. The computer system of claim 15, wherein the text mining further comprises inferring, from the references, a semantic similarity between the references.

20. The computer system of claim 19, wherein the semantic similarity is between a name of a third biomolecule affected by the pharmaceutical and a name of a fourth biomolecule affected by at least one of the first and second diseases, and wherein the names are from the references.

* * * * *